United States Patent [19]

Hansen

[11] Patent Number: 5,330,990

[45] Date of Patent: Jul. 19, 1994

[54] SUBSTITUTED UREA COMPOUNDS AND THEIR PREPARATION AND USE

[75] Inventor: John B. Hansen, Lyngby, Denmark

[73] Assignee: Novo Nordisk A/S, Bagsvaerd, Denmark

[21] Appl. No.: 947,073

[22] Filed: Sep. 17, 1992

Related U.S. Application Data

[63] Continuation of Ser. No. 573,934, Aug. 27, 1990, abandoned.

[30] Foreign Application Priority Data

Sep. 8, 1989 [DK] Denmark .............................. 4434/89

[51] Int. Cl.[5] ..................... A61K 31/44; C07D 221/02
[52] U.S. Cl. .................................. 514/299; 514/304; 546/112; 546/124; 546/125
[58] Field of Search ...................... 546/124, 112, 125; 514/304, 299

[56] References Cited

FOREIGN PATENT DOCUMENTS 0158265 10/1985 European Pat. Off. .
0235878 9/1987 European Pat. Off. .
0323077 12/1988 European Pat. Off. .

Primary Examiner—Howard T. Mars
Assistant Examiner—Catherine Scalzo
Attorney, Agent, or Firm—Steve T. Zelson; Elias J. Lambiris

[57] ABSTRACT

New substituted urea compounds of formula I, or a pharmaceutically acceptable salt thereof:

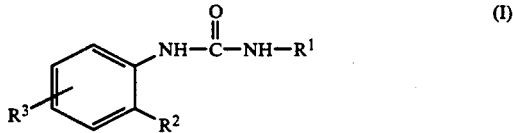

wherein
$R^1$ is a group of formula II, III or IV

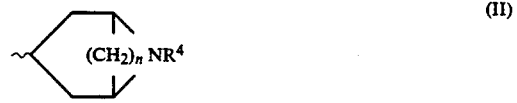

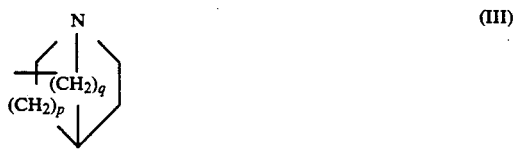

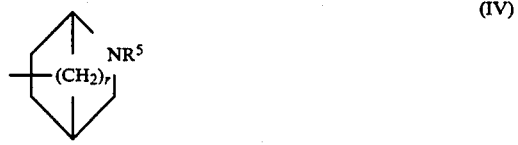

where n is 2 or 3, p is 1 or 2, q is 1 to 3, r is 1-3 and $R^4$ and $R^5$ are H, $C_{1-7}$ alkyl or $C_{3-6}$ cycloalkyl; and wherein $R^2$ is an oxadiazole, substituted with $C_1$ alkyl, $C_{2-8}$ alkenyl, $C_{2-8}$ alkynyl, $C_{3-7}$ cycloalkyl, benzyl, phenyl, $C_{1-6}$ alkoxy, $C_{1-6}$ alkylthio, amino or alkylamino; or wherein $R^2$ —C—$R^6$=—N—O—$R^7$ wherein $R^6$ is hydrogen or methyl and $R^7$ is $C_{1-6}$ alkyl which may be substituted with $C_{3-7}$ cycloalkyl;

and wherein $R^3$ is hydrogen, halogen, nitro, substituted amine, trifluoromethyl, $C_{1-6}$ alkyl or $C_{1-6}$ alkoxy.

The compounds are useful in pharmaceutical preparations for treating psychotic disorders, nausea and vomiting.

14 Claims, No Drawings

SUBSTITUTED UREA COMPOUNDS AND THEIR PREPARATION AND USE

This application is a continuation application of application Ser. No. 07/573,934, filed Aug. 27, 1990 abandoned.

The present invention relates to therapeutically active substituted urea compounds, a method of preparing the same, pharmaceutical compositions comprising the compounds, and a method of treating therewith.

EP158265 and EP 235878 describes benzamides and substituted urea compounds having an azabicyclic side chain and possesing 5-HT antagonist activity.

A class of novel, structurally distinct compounds with higher $5HT_3$ - antagonist activity has now been discovered. These compounds have $5\text{-}HT_3$-receptor antagonist activity, anti-emetic activity and/or gastric motility enhancing activity.

The present invention provides a compound of formula I, or a pharmaceutically acceptable salt thereof:

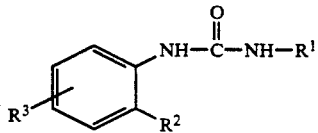

(I)

wherein
$R^1$ is a group of formula II, III or IV

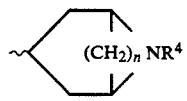

(II)

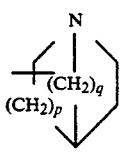

(III)

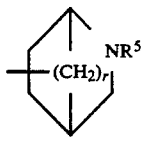

(IV)

where n is 2 or 3, p is 1 or 2, q is 1 to 3, r is 1-3 and $R^4$ and $R^5$ are H, $C_{1\text{-}7}$ alkyl or $C_{3\text{-}6}$ cycloalkyl; and wherein $R^2$ is an oxadiazole, substituted with $C_{1\text{-}8}$ alkyl, $C_{2\text{-}8}$ alkenyl, $C_{2\text{-}8}$ alkynyl, $C_{3\text{-}7}$ cycloalkyl, benzyl, phenyl, $C_{1\text{-}6}$ alkoxy, $C_{1\text{-}6}$ alkylthio, amino or alkylamino; or wherein $R^2$ is $-C-R^6=N-O'R^7$ wherein $R^6$ is hydrogen or methyl and $R^7$ is $C_{1\text{-}6}$ alkyl which may be substituted with $C_{3\text{-}7}$ cycloalkyl;

and wherein $R^3$ is hydrogen, halogen, nitro, substituted amines, trifluoromethyl, $C_{1\text{-}6}$ alkyl or $C_{1\text{-}6}$ alkoxy.

The invention also provides a process for the preparation of a compound of formula (I), or a pharmaceutically acceptable salt thereof, which process comprises reacting a compound of formula V:

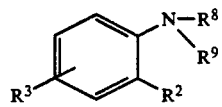

(V)

with a compound of formula VI $J-R^1$ where $R^1$, $R^2$, $R^3$ are as defined above.

$R^8$ is COQ, where Q is a group displaceable by a nucleophile, $^8$ and $R^9$ together =C=O, or $R^8$ is hydrogen (when $R^9$ is hydrogen); and when $R^8$ is COQ, or $R^8-N-R^9$ is N=C=O, J is $NH_2$, or a reactive derivative thereof or when $R^8$ is hydrogen, J is a group containing an activated carbonyl group capable of forming a CO—N-linkage with the compound of formula (V).

Pharmaceutically acceptable salts of the compounds of this invention may be formed conventionally. The acid addition salts may be formed for example by reaction of the base compound of formula (I) with a pharmaceutically acceptable organic or inorganic acid.

Compounds of formula (I), which antagonise the effect of 5-HT at $5\text{-}HT_3$ receptors, are useful in the treatment of conditions such as psychotic disorders (e.g. schizophrenia and mania); anxiety; and nausea and vomiting, particularly that associated with cancer chemotherapy and radiotherapy. Compounds of formula (I) are also useful in the treatment of gastric tasis; symptoms of gastrointestinal dysfunction such as occur with dyspepsia, peptic ulcer, reflux oesophagitis, flatulence and irritable bowel syndrome; migraine; and pain. Compounds of formula (I) may also be used in the treatment of dependency on drugs and substances of abuse, depression, and dementia and other cognitive disorders.

Unlike existing drug treatments for certain of the above conditions, the compounds of the invention, because of their high selectivity for $5\text{-}HT_3$ receptors, would not be expected to produce undesirable side effects. Thus, for example, neuroleptic drugs may cause extrapyramidal effects, such as tardive dyskinesia, and benzodiazepines may cause dependence.

According to another aspect, the invention provides a method of treatment of a human or animal subject suffering from a psychotic disorder such as schizophrenia or mania; or from anxiety; nausea or vomiting, particularly that associated with cancer chemotherapy and radiotherapy; gastric stasis; symptoms of gastrointestinal dysfunction such as dyspepsia, reflux oesophagitis, peptic ulcer, flatulence and irritable bowel syndrome; migraine; pain; dependency on drugs or substances of abuse; depression; or dementia and other cognitive disorders which comprises administering an effective amount of a compound of formula (I) or a physiologically acceptable salt or solvate thereof.

Compounds of formula (I) were tested for their $5HT_3$-antagonist activity using the following method:

Principle

5-HT produces contractions of the guinea pig ileum via 2 different receptors. 1) direct contractions via $5\text{-}HT_2$ receptors on the muscle, 2) indirect contractions via $5\text{-}HT_3$ recaptots on intrinsic gut neurones, producing acetylcholine release. By administering 5-HT to lengths of ileum in the presence of methysergide (to block 5-HT$_2$ receptors) you can assay 5-HT$_3$ receptor activity.

Method

Guinea pigs were killed by means of cervical dislocation the terminal 15 cm of ileum removed, and 1.5–2.0 cm lengths prepared and mounted in 10 ml organ baths containing calcium deficient tyrodes of the following composition (mM) NaCl (136.9); KCl (2.68); CaCl$_2$ (0.9); MgCl$_2$ (1.05); NaCO$_3$ (11.9); NaH$_2$PO$_4$ (0.42); glucose (5.55) and containing methysergide (10$^{-6}$M) maintained at 37° C. and gassed with 95% O$_2$ and 5% CO$_2$. The mechanical activity of the muscle was measured by a HSE 351 isometric transducer connected via a HSE bridge amplifier to a potentiometric pen recorder. Resting tension was 1 g and the tissue left to equilibrate for 1 hour.

First a dose response curve is obtained to acetylcholine on each tissue. Then one tissue is incubated for 20 min with tyrode and three with tyrode plus the putative 5-HT$_3$ antagonist. After this incubation dose response curves to 5-HT are constructed to 5-HT in all 4 tissues (one control 3+test drug). Contact time for 5-HT 30 sec.

Results

The maximum response to acetylcholine for each tissue is measured and the responses to 5-HT calculated as percentage maximum of the acetylcholine (Ach) maximum response in that tissue. The peak of the 5-HT response is measured.

For each tissue the concentration of 5-HT giving 100% of the maximum acetylcholine response (measured at 30 sac) is quoted.

The effect of a drug is quantified as the ratio of the concentration of 5-HT producing a 100% maximal Ach response in the presence and absence of the antagonist (dose ratio). The figure quoted is the concentration of the antagonist giving a dose ratio of 2, (A$_2$).

Test results obtained by testing some compounds of the invention appear from table I

TABLE I

| EXAMPLE NO | A$_2$ µg/ml |
|---|---|
| 5 | 0.016 |
| 6 | 0.1 |
| 18 | 0.012 |
| 8 | 0.0013 |
| 10 | 0.1 |
| 11 | 0.01 |
| 7 | 0.005 |
| 15 | 0.0018 |
| 16 | 0.012 |

The compound of the invention, together with a conventional adjuvant, carrier, or dihent, and if desired in the form of a pharmaceutically-acceptable acid addition salt thereof, may be placed into the form of pharmaceutical compositions and unit dosages thereof, and in such form may be employed as solids, such as tablets or filled capsules, or liquids, such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective central nervous system ailment alleviating amount of the active ingredient commensurate with the intended daily dosage range to be employed. Tablets containing one (1) milligram of active ingredient or, more broadly, one (1) to thirty (30) milligrams, per tablet, are accordingly suitable representative unit dosage forms.

The compounds of this invention can thus be used for the formulation of pharmaceutical preparations, e.g., for oral and parenteral administration to mammals including humans, in accordance with conventional methods of galenic pharmacy.

Conventional excipients are such pharmaceutically acceptable organic or inorganic carrier substances suitable for parenteral or oral application which do not delteriously react with the active compound.

Examples of such carriers are water, salt solutions, alcohols, polyethylene glycols, polyhydroxyethoxylated castor oil, gelatin, lactose, amylose, magnesium stearate, talc, silicic acid, fatty acid monoglycerides and diglycerides, pentaerythritol fatty acid esters, hydroxymethylcelhlose and polyvinylpyrrolidone.

The pharmaceutical preparations can be sterilized and mixed, if desired, with auxilliary agents, such as lubricants, preservatives, stabilizers, wetting agents, emulsifiers, salt for influencing osmotic pressure, buffers and/or coloring substances and the like, which do not deleteriously react with the active compound.

For parenteral application, particularly suitable are injectable solutions or suspensions, preferably aqueous solutions with the active compound dissolved in polyhydroxylated castor oil.

Ampoules are convenient unit dosage forms.

For oral application, particularly suitable are tablets, dragees, or capsules having talc and/or a carbohydrate carrier or binder or the like, the carrier preferably being lactose and/or corn starch aM/or potato starch. A syrup, elixir or like can be used when a sweetened vehicle can be employed. Generally, as to broader ranges, the compound of the invention is dispensed in unit dosage form comprising 0.05–100 mg in a pharmaceutically-acceptable carrier per unit dosage.

A typical tablet which may be prepared by conventional tabletting techniques contains:

| | |
|---|---|
| Active compound | 1.0 mg |
| Lactosum | 67.9 mg ph. Eur. |
| Avicel ® | 31.4 mg |
| Amberlite ® IRP 88 | 1.0 mg |
| Magnesii stearas | 0.25 mg Ph. Eur. |

The invention will now be described in further detail with reference to the following examples:

EXAMPLE 1

5-(2-Aminophenyl)-3-cyclopropyl-1,2,4-oxadiazole

Methyl 2-amino-benzoate (6 g, 40 mmol) and cyclopropylcarboxamid oxime (5 g, 50 mmol) was refluxed for 10 h in dry ethanol containing 0.25 g sodium and 2 g molecular sieves. The mixture was filtered while hot, and cooled precipitating 2.8 g of the desired product as white needles. Upon addition of water to the flitrate, a further amount of 3.2 g white crystals could be isolated. M.p. 84.4°–84.9° C.

By a similar procedure were prepared:
5-(2-aminophenyl)-3-methyl-1,2,4-oxadiazol. M.p. 118.2°–119.8° C., 5- (2-amtnophenyl) -3-phenyl- 1,2,4-oxadiazol. M.p. 128°-129° C.,
5-(2-aminophenyl)-3-butyl-1,2,4-oxadiazol. M.p. 36.4°-36.6° C.,
5- (2-amino-6-chlorophenyl) -3-cyclopropyl- 1,2,4-oxadiazol. M.p. 103°-105° C.,
5- (2-amino-4-chlorophenyl) -3-cyclopropyl- 1,2,4-oxadiazol. M.p. 135°-136° C. and
5-(2-amino-3-methylphenyl)-3-cyclopropyl-1,2,4-oxadiazol. M.p. 137°-138° C.

EXAMPLE 2

2- (N-Methoxyiminomethyl)-trobenzene

To 2-nitrobenzaldehyde (10 g, 66 mmol) in 200 ml DMF was added O-methylhydroxylamine. HCl (8.3 g, 0.1 mol) and NaHCO$_3$/8.4 g, 0.1 mol). The mixture was then stirred at 80° C. for two h and concentrated in vacuo to a small volume. By addition of H$_2$O crystallized the desired compound. Recrystallization from H$_2$O gave 12 g white crystals. M.p. 44°-45° C.

EXAMPLE 3

2 - Amino-N-methoxyiminome thylbenzene 2-(N-methoxyiminomethyl)-nitrobenzene (6.5 g) in 350 ml 99.9% ethanol was reduced catalytically at room temperature, 1 atm. using 0.7 g 10% Pd on carbon. Upon completion of the reduction the solution was filtered through filter aid and concentrated in vacuo. The product was redissolved in methylene chloride and filtered through silicagel. Evaporation of the solvent gave the desired product as an oil.

By a similar procedure were prepared:
2-amino-N-ethoxyiminomethylbenzene, oil
2-amino-N-cyclopropylmethoxyiminomethylbenzene, oil.
2-amino-N-isopropoxyiminomethylbenzene, oil.

EXAMPLE 4

2-(2-Aminophenyl)-5-methyl-1,3,4-oxadiazol

A mixture of isatoic anhydride (16.3 g, 0.1 mol), p-toluenesulfonic acid (0.2 g, 1.1 mmol), glacial acetic acid (10 ml), acethydrazide (7.4 g, 0.1 mol) and dry toluene (90 ml) was stirred at 120° C. for 4 h, cooled to room temperature and poured into ice water. Toluene (500 ml) was added, and the phases were separated. The aqueous phase was extracted with CH$_2$Cl$_2$ (2×100 ml).

The combined organic phases were dried and concentrated in vacuo. The resulting oil was dissolved in warm ethylacetate. By cooling and addition of ether the desired product precipitated, 3.4 g. M.p. 152°-158° C.

By similar procedures were prepared:
2-(2-aminophenyl)-1,3,4-oxadiazol. M.p. 206°-209° C.
2-(2-aminophenyl)-5-butyl-1,3,4-oxadiazol. M.p. 89°-92° C.
2-(2-aminophenyl)-5-phenyl-1,3,4-oxadiazol. M.p. 163°-170° C.

EXAMPLE 5

N-(2-(3-Cyclopropyl-1,2,4-oxadiazol-5-yl)phenyl)-N$^1$-(endo-8-methyl-8-azabicyclo[3.2.1]oct-3-yl)urea HCl To a solution of phosgene in toluene (8.5 ml, 2.6M) stirred under N$_2$ at 0° C. was added dropwise 5-(2-aminophenyl)-3-cyclopropyl-1,2,4-oxadiazole (3.0 g, 20 mmol) in 175 ml dry methylene chloride. After 100 ml of the solution was added 6.5 ml of dry triethylamine was added. Upon addition the mixture was stirred at 0° C. for 15 min. whereupon a solution of (endo)- 8-methyl-8-azabicyclo[3.2.1]octan-3-amine (2.8 g, 20 mmol) in 10 ml CH$_2$Cl$_2$ was added. This mixture was stirred at room temperature for 3 h and washed with 150 ml saturated sodium bicarbonate. The organic phase was dried with magnesium sulphate and concentrated in vacuo. The resulting oil was recrystallized three times from ethyl acetate to give 1.3 g of the desired product as white crystals. This product was dissolved in ethanol and precipitated as the hydrochloride by addition of dry hydrochloric acid in ether, giving 1.3 g. M.p. 178°-80° C.

EXAMPLE 6

N-(Endo-8-methyl-8-azabicyclo[3.2.1]oct-3-yl) -N$^1$-(2-(3-methyl-1,2,4-oxadiazol-5-yl)-phenyl)urea, HCl To a solution of phosgene in toluene (4 ml, 2.6M) stirred under N$_2$ at 0° C. was added dropwise 5-(2-aminophenyl)-3-methyl-1,2,4-oxadiazol (1.4 g, 8 mmol) in 100 ml dry methylene chloride. After 50 ml of the solution was added, 2.8 ml of dry triethylamine was added. Upon addition the mixture was stirred at 0° C. for 15 min. whereupon a solution of (endo)-8-methyl-8-azabicyclo[3.2.1octan-3-amine (1.1 g, 8 mmol) in 10 ml CH$_2$Cl$_2$ was added. This mixture was stirred at room temperature for 3 h and washed with 150 ml saturated sodium bicarbonate. The organic phase was dried with magnesium sulphate and concentrated in vacuo. The resulting oil was recrystallized three times from ethylacetate to give 1.0 g of the desired product as white crystals. This product was dissolved in ethanol and precipitated as the hydrochloride by addition of dry hydrochloric acid in ether, giving 0.76 g. M.p. 156°-160° C.

EXAMPLE 7

N-(2-(3-Butyl-1,2,4-oxadiazol-5-yl)phenyl )-N$^1$-(endo-8-methyl-8-azabicyclo[3.2.1]oct-3-yl)urea, (CO$_2$H)$_2$ To a solution of phosgene in toluene (6.5 ml, 1.93M) stirred under N$_2$ at 0° C. was added dropwise 5-(2-aminophenyl)-3-butyl- 1,2,4-oxadiazol (1.3 g, 6 mmol) in 50 ml dry methylene chloride. After 25 ml of ml of dry triethylamine was added. Upon addition the mixture was stirred at 0° C. for 15 min. whereupon a solution of (endo)-8-methyl-8-azabicyclo[3.2.1]octan-3-amine (1.0 g, 7 mmol) in 5 ml CH$_2$Cl$_2$ was added. This mixture was stirred at room temperature for 20 h and washed with 50 ml saturated sodium bicarbonate, 50 ml water, and 50 ml saturated sodium chloride. The organic phase was dried with magnesium sulphate and concentrated in vacuo. The resulting oil dissolved in acetone (5 ml) and treated with oxalic acid (0.6 g) in 5 ml acetone to give 0.6 g of the desired product as white crystals. M.p. 180°-181° C.

EXAMPLE 8

N-(2-(3-Cyclopropyl-1,2,4-oxadiazol-5-yl)-phenyl)-N$^1$-(endo-9-methyl-9-azabicyclo[3.3.1 ]non-3-yl)urea, HCl To a solution of phosgene in toluene (4.7 ml, 1.93M) stirred under N$_2$ at 0° C. was added dropwise 5-(2-aminophenyl)-3-cyclo-propyl-1,2,4-oxadiazol (1.6 g, 8 mmol) in 100 ml dry methylene chloride. After 50 ml of the solution was added, 2.5 ml of dry triethylamine was added. Upon addition the mixture was stirred at 0° C. for 15 min. whereupon a solution of (endo)-9-methyl-9- azabicyclo[3.3.1]nonan-3-amine (1 g, 6.4 mmol) in 10 ml CH$_2$Cl$_2$ was added. This mixture was stirred at room temperature for 3 h and washed with 50 ml saturated sodium bicarbonate. The organic phase was dried with magnesium sulphate and concentrated in vacuo. The resulting oil was dissolved in methanol. Addition of ether gave 1.8 g of the desired product as white crystals. This product was dissolved in ethanol and precipitated as the hydrochloride by addition of dry hydrochloric acid in ether, giving 1.4 g of the desired product. M.p. 145°–147,5° C.

EXAMPLE 9

N-(Endo-8-methyl-8-azabicyclo[3.2.1]oct-3-yl)-N$^1$-(2-(3-phenyl-1,2,4-oxadiazol-5-yl)-phenyl)urea, HCl To a solution of phosgene in toluene (8.5 ml, 1.9M) stirred under N$_2$ at 0° C. was added dropwise 5-(2-aminophenyl)-3-phenyl- 1,2,4-oxadiazol (1.9 g, 8 mmol) in 50 ml dry methylene chloride. After 25 ml of the solution was added, 3.5 ml of dry triethylamine was added. Upon addition the mixture was stirred at 0° C. for 15 min. whereupon a solution of (endo)- 8-methyl-8-azabicyclo[3.2.1]octan-3-amine (1.4 g, 10 mmol) in 10 ml CH$_2$Cl$_2$ was added. This mixture was stirred at room temperature for 20 h and washed with 50 ml saturated sodium bicarbonate, 50 ml water and 50 ml saturated sodium chloride. The organic phase was dried with magnesium sulphate and concentrated in vacuo. The resulting product was washed with acetone, dissolved in ethanol and precipitated as the hydrochloride by addition of dry hydrochloric acid in ether. Recrystallization from ethanol and methanol gave 0.9 g of the desired product. M.p. 281°–282° C.

EXAMPLE 10

N-(2-(3-Cyclopropyl-1,2,4-oxadiazol-5-yl)-phenyl)-N$^1$-(3-quinuclidinyl)urea

To a solution of phosgene in toluene (1.5 ml, 1.9M) stirred under N$_2$ at 0° C. was added dropwise 5-(2-aminophenyl)-3-cyclopropyl-1,2,4-oxadiazol (0.5 g, 2.5 mmol) in 30 ml dry methylene chloride and then 0.8 ml of dry triethylamine. Upon addition the mixture was stirred at 0° C. for 15 min. whereupon a solution of 3-aminoquinuclidine (0.18 g, 1.4 mmol) in 10 ml CH$_2$Cl$_2$ was added. This mixture was stirred at room temperature for 4 h and washed with 25 ml saturated sodium bicarbonate. The organic phase was dried with magnesium sulphate and concentrated in vacuo. The resulting oil dissolved in methanol. Addition of ether precipitated 0.38 g of the desired product as white crystals. This product was dissolved in ethanol and precipitated as the hydrochloride by addition of dry hydrochloric acid in ether, giving 0.3 g. M.p. 229°–233° C.

EXAMPLE 11

N-(Endo-9-methyl-9-azabicyclo[3.3.1]non-3-yl)-N$^1$-(2-(3-phenyl-1,2,4-oxadiazol-5-yl)phenyl)urea To a solution of phosgene in toluene (17 ml, 1.9M) stirred under N$_2$ at 0° C. was added dropwise 5-(2-aminophenyl )-3-phenyl-1,2,4-oxadiazol (3.8 g, 16 mmol) in 100 ml dry methylene chloride. After 50 ml of the solution was added, 7 ml of dry triethylamine was added. Upon addition the mixture was stirred at 0° C. for 15 min. whereupon a solution of (endo)-9-methyl-9-azabicyclo[3.3.1]nonan-3-amine (1.5 g, 10 mmol) in 10 ml CH$_2$Cl$_2$ was added. This mixture was stirred at room temperature for 24 h and washed with 50 ml saturated sodium bicarbonate, 50 ml H$_2$O and 50 ml saturated sodium chloride. The product was triturated with methanol to give 1.0 g of the desired compound. M.p. 182°–185° C.

EXAMPLE 12

N-(2-(3-Butyl-1,2,4-oxadiazol-5-yl)phenyl)-N$^1$-(endo-9-methyl-9-azabicyclo[3.3.1]non-3-yl)urea, HCl To a solution of phosgene in toluene (6.5 ml, 1.9M) stirred under N$_2$ at 0° C. was added dropwise 5-(2-aminophenyl)-3-butyl-1,2,4-oxadiazol (1.43 g, 6 mmol) in 50 ml dry methylene chloride. After 25 ml of the solution was added, 1.7 ml of dry triethylamine was added. Upon addition the mixture was stirred at 0° C. for 15 min. whereupon a solution of (endo)-9-methyl-9-azabicyclo[3.3.1]nonan-3-amine (1.1 g, 7 mmol) in 5 ml CH$_2$Cl$_2$ was added. This mixture was stirred at room temperature for 24 h and washed with 50 ml saturated sodium bicarbonate and 50 ml water. The organic phase was dried with magnesium sulphate and concentrated in vacuo. This product was dissolved in ethanol and precipitated as the hydrochloride by addition of dry hydrochloric acid in ether. Recrystallization from ethanol gave 1.7 g of the desired product duct as white crystals. M.p. 217°–218° C.

EXAMPLE 13

N-(3-Chloro-2-(3-cyclopropyl-1,2,4-oxadtazol-5-yl)-phenyl)-N$^1$-( endo-9-methyl-9-azabicyclo[3.3.1]non-3-yl)urea To a solution of phosgene in toluene (9 ml, 1.9M) stirred under N$_2$ at 0° C. was added dropwise 5-(2-amino-6-chlorophenyl)-3-cyclopropyl-1,2,4-oxadiazol (2.0 g, 8.5 mmol) in 60 ml dry methylene chloride. After 30 ml of the solution was added, 4.8 ml of dry triethylamine was added. Upon addition the mixture was stirred at 0° C. for 15 min. whereupon a solution of (endo)-9-methyl-9-azabicyclo[1.3.3]nonan-3-6.2 mmol) in 10 ml CH$_2$Cl$_2$ was added. This mixture was stirred at room temperature for 24 h and washed with 150 ml saturated sodium bicarbonate. The organic phase was dried with magnesium sulphate and concentrated in vacuo. The resulting oil was treated with acetone to give 1.3 g of the desired product as white crystals. M.p. 199°–203° C.

EXAMPLE 14

N-(5-Chloro-2-(3-cyclopropyl-1,2,4-oxadiazol-5-yl )-phenyl)-N$^1$-(endo-9-methyl-9-azabicyclo[3.3.1]non-3-yl)urea To a solution of phosgene in toluene (4.2 ml, 1.9M) stirred under N$_2$ at 0° C. was added dropwise 5-(2-emino-4-chlorophenyl)-3-cyclopropyl-1,2,4-oxadiazol (1 dry methylene chloride. After 20 ml of the solution was added, 2.4 ml of dry triethylamine was added. Upon addition the mixture was stirred at 0° C. for 15 min. whereupon a solution of (endo)-9-methyl-9-azabicyclo[3.3.1](1 g, 6.5 mmol) in 10 ml CH$_2$Cl$_2$ was added. This mixture was stirred at room temperature for 3 h and washed with 150 ml saturated sodium bicarbonate. The organic phase was dried with magnesium sulphate and concentrated in vacuo. The resulting oil was recrystallized from ethanol to give 0.9 g of the desired product as white crystals. M.p. 196°–197° C.

EXAMPLE 15

N-(Endo-8-methyl-8-azabicyclo[3.2.1]oct-3-yl)-N¹-(2-(N-cyclo-propylmethoxyiminomethyl)phenyl)urea, HCl To a solution of phosgene in tolene (3 ml, 1.9M) stirred under $N_2$ at 0° C. was added dropwise 2-amino-N-cyclopropyl-methoxyiminomethylbenzene (0.47 g, 2.5 mmol) in 25 ml dry methylene chloride and then 0.8 ml of dry triethylamine. Upon addition the mixture was stirred at 0° C. for 15 min. whereupon a solution of (endo)-8-methyl-8-azabicyclo-[3.2.1]octan-3-amine (0.2 g, 1.4 mmol) in 5 ml $CH_2Cl_2$ was added. This mixture was stirred at 40° C. for 30 h and washed with 150 ml saturated sodium bicarbonate. The organic phase was dried with magnesium sulphate and concentrated in vacuo. The resulting oil was purified by column chromatography (silicagel; methanol, triethylamine (100:1)). This product was dissolved in ethanol and precipitated as the hydrochloride by addition of dry hydrochloric acid in ether, giving 0.1 g. M.p. 127° C. (dec.).

EXAMPLE 16

N-(Endo-8-methyl-8-azabicyclo[3.2.1]oct-3-yl)-N¹-(2-(N-ethoxyiminomethyl)phenyl)urea, HCl To a solution of phosgene in toluene (3 ml, 1.9M) stirred under $N_2$ at 0° C. was added dropwise 2-amino-N-ethoxyimino-methylbenzene (0.41 g, 2.5 mmol) in 25 ml dry methylene chloride and then 0.8 ml of dry triethylamine. Upon addition the mixture was stirred at 0° C. for 15 min. whereupon a solution of ( endo )-8-methyl-8-azabicyclo[3.2.1]octan-3-amine (0.2 g, 1.4 mmol) in 5 ml $CH_2Cl_2$ was added. This mixture was stirred at 40° C. 30 h and washed with 150 ml saturated sodium bicarbonate. The organic phase was dried with magnesium sulphate and concentrated in vacuo. The resulting oil was purified by column chromatography (silica-gel; methanol, triethylamine (100:1)). This product was dissolved in ethanol and precipitated as the hydrochloride by addition of dry hydrochloric acid in ether, giving 0.23 g. M.p. 165°–178° C. (dec.).

EXAMPLE 17

N-(2-(N-Methoxytmtnomethyl)phenyl)-N¹-(endo-8-methyl-8-azabicyclo[3.2.1]oct-3-yl)urea, HCl To a solution of phosgene in toluene (4 ml, 2.6M) stirred under $N_2$ at 0° C. was added dropwise 2-amino-N-methoxyimino-methylbenzene (1.4 g, 9.3 mmol) in 90 ml dry methylene chloride. After 45 ml of the solution was added, 3 ml of d triethylamine was added. Upon addition the mixture was stirred at 0° C. for 15 min. whereupon a solution of (endo)-8-methyl-8-azabicyclo[3.2.1]octan-3-amine (2.8 g, 20 mmol) in 10 ml $CH_2Cl_2$ was added. This mixture was stirred at room temperature for 20 h and washed with 150 ml saturated sodium bicarbonate. The organic phase was dried with magnesium sulphate and concentrated in vacuo. The resulting oil was purified by column chromatography (silicagel; methanol, triethylamine (100:1)). This product was dissolved in acetone and precipitated as the hydrochloride by addition of dry hydrochloric acid in ether, giving 0.14 g. M.p. 152°–153° C.

EXAMPLE 18

N-(2-(N-Methoxyiminomethyl)phenyl)-N¹-(endo-9-methyl-9-azabicyclo[3.3.1]non-3-yl)urea To a solution of phosgene in toluene (4 ml, 2.6M) stirred under $N_2$ at 0° C. was added dropwise 2-amtno-N-methoxyiminomethylbenzene (1.4 g, 9.3 mmol) in 90 ml dry methylene chloride. After 45 ml of the solution was added, 3 ml of dry triethylamine was added. Upon addition the mixture was stirred at 0° C. for 15 min. whereupon a solution of (endo)-9-methyl-9-azabicyclo[3.3.1]nonan-3-amine (3.1 g, 20 mmol) in 10 ml $CH_2Cl_2$ was added. This mixture was stirred at room temperature for 24 h and washed with 150 ml saturated sodium bicarbonate. The organic phase was dried with magne-sium sulphate and concentrated in vacuo. The resulting oil was recrystallized from ethylacetate to give 0.4 g of the desired product as white crystals. M.p. 150°–151° C.

EXAMPLE 19

N-(Endo-9-methyl-9-azabicyclo[3.3.1]non-3-yl)-N¹-(2-(2-methyl-1,3,4-oxadiazol-5-yl)-phenyl )urea, HCl To a solution of phosgene in toluene (2.4 ml, 1.93M) stirred under $N_2$ at 0° C. was added dropwise 2-(2-aminophenyl)-5-methyl-1,3,4-oxadiazol (0.71 g, 4.1 mmol) in 50 ml dry methylene chloride. After the solution was added, 1.3 ml of dry triethylamine was added. Upon addition the mixture was stirred at 0° C. for 15 min. whereupon a solution of (endo)-9-methyl-9-azabicyclo[3.3.1]nonan-3-amine (0.52 g, 3.4 mmol) in 10 ml $CH_2Cl_2$ was added. This mixture was stirred at room temperature for 3 h and washed with 150 ml saturated sodium bicarbonate. The organic phase was dried with magnesium sulphate and concentrated in vacuo. The resulting oil was purified by column chromatography (methanol; triethylamine (100:1)) to give 0.54 g of the desired product as white crystals. This product was dissolved in methanol and precipitated as the hydrochloride by addition of dry hydrochloric acid in ether, giving 0.47 g. M.p. 156°–160° C.

EXAMPLE 20

N-(Endo-9-methyl-9-azabicyclo[3.3.1]non-3-yl)-N¹-(2-(1,3,4-oxadiazol-2-yl)-phenyl)urea, To a solution of phosgene in toluene (2.4 ml, 1.93M) stirred under $N_2$ at 0° C. was added dropwise 2-(2-aminophenyl)-1,3,4-oxadiazol (0.65 g, 4.3 mmol) in 50 ml dry methylene chloride. After the solution was added, 1.3 ml of dry triethylamine was added. Upon addition the mixture was stirred at 0° C. for 15 min. whereupon a solution of (endo)- 9-methyl-9-azabicyclo[3.3.1]nonan-3-amine (0.52 g, 3.4 mmol) in 10 ml $CH_2Cl_2$ was added. This mixture was stirred at room temperature for 3 h and washed with 150 ml saturated sodium bicarbonate. The organic phase was dried with magnesium sulphate and concentrated in vacuo. The resulting oil was purified by column chromatography (silicagel; methanol, triethylamine (100:1)) to give 0.32 g of the desired product as white crystals. This product was dissolved in methanol and precipitated as the hydrochloride by addition of dry hydrochloric acid in ether, giving 0.25 g. M.p. 156°–160° C.

EXAMPLE 21

N-(Endo-8-methyl-8-azabicyclo[3.2.1]oct-3-yl)-N$^1$-(2-(2-methyl-1,3,4-oxadiazol-5-yl)-phenyl)urea, HCl To a solution of phosgene in toluene (2.4 ml, 1.9M) stirred under N$_2$ at 0° C. was added dropwise 2-(2-aminophenyl)-5-methyl- 1,3,4-oxadiazol (0.71 g, 4.1 mmol) in 50 ml dry methylene chloride. After 25 ml of the the solution was added, 1.3 ml of dry triethylamine was added. Upon addition the mixture was stirred at 0° C. for 15 min. whereupon a solution of (endo)- 8-methyl-8-azabicyclo[3.2.1]octan-3-amine (0.47 g, 3.4 mmol) in 10 ml CH$_2$Cl$_2$ was added. This mixture was stirred at room temperature for 3 h and washed with 150 ml saturated sodium bicarbonate. The organic phase was dried with magnesium sulphate and concentrated in vacuo. The resulting oil was purified by column chromatography (silicagel; methanol triethylamine (100:1)). This product was dissolved in methanol and precipitated as the hydrochloride by addition of dry hydrochloric acid in ether, giving 0.2 g. M.p. 155° C. (dec.).

EXAMPLE 22

N-(Endo-8-methyl-8-azabicyclo[3.2.1]oct-3-yl)-N$^1$-(2-(1,3,4-oxadiazol-2-yl)-phenyl)urea, HCl To a solution of phosgene in toluene (2.4 ml, 1.9M) stirred under N$_2$ at 0° C. was added dropwise 2-(2-aminophenyl)-1,3,4-oxadiazol (0.65 g, 4.0 mmol) in 50 ml dry methylene chloride. After 25 ml of the solution was added, 1.3 ml of dry triethylamine was added. Upon addition the mixture was stirred at 0° C. for 15 min. whereupon a solution of (endo)- 8-methyl-8-azabicyclo[3.2.1]octan-3-amine (0.49 g, 3.5 mmol) in 10 ml CH$_2$Cl$_2$ was added. This mixture was stirred at room temperature for 4 h and washed with 150 ml saturated sodium bicarbonate. The organic phase was dried with magnesium sulphate and concentrated in vacuo. The resulting oil was purified by column chromatography (silicagel; methanol, triethylamine (100:1)). This product was dissolved in methanol and precipitated as the hydrochloride by addition of dry hydrochloric acid in ether, giving 0.6 g. M.p. 125° C. (dec.).

EXAMPLE 23

N-(2-(2-Butyl-1,3,4-oxadiaxol-5-yl)phenyl)-N$^1$-(endo-9-methyl-9-azabicyclo[3.3.1]non-3-yl)urea, oxalate To a solution of phosgene in toluene (3.4 ml, 1.93M) stirred under N$_2$ at 0° C. was added dropwise 2-(2-aminophenyl)-5-butyl- 1,3,4-oxadiazol (0.5 g, 2.3 mmol) in 15 ml dry methylene chloride and 0.9 ml of dry triethylamine. Upon addition the mixture was stirred at 0° C. for 15 min. whereupon a solution of (endo)-9-methyl-9-azabicyclo[3.3.1](0.4 g, 2.6 mmol) in 10 ml CH$_2$Cl$_2$ was added. This mixture was stirred at room temperature for 20 h and washed with 25 ml saturated sodium bicarbonatesolution. The organic phase was dried with magnesium sulphate and concentrated in vacuo. The resulting oil was dissolved in acetone and precipitated as the oxalate by addition of oxalic acid in acetone. Recrystallization from ethanol and ether gave 0.4 g of the desired product. M.p. 95° C. (dec.).

EXAMPLE 24

N-(Endo-9-methyl-9-azabicyclo [3.3.1]non-3-yl)-N$^1$-(2-(3-cyclopropyl-1,2,4-oxadiazol-5-yl)-6-methylphenyl)urea To a solution of phosgene in toluene (5.2 ml, 1.9M) stirred under N$_2$ at 0° C. was added dropwise a mixture of 5-(2-amino-3-methylphenyl)-3-cyclopropyl-1,2,4-oxadiazol (1.1 g, 5 mmol) and 1.4 ml of dry triethylamine in 25 ml dry methylene chloride. Upon addition the mixture was stirred at 0° C. for 1 hour and at room temperature for 2 hours. The mixture was then concentrated in vacuo and redissolved in 25 ml dry methylene chloride and 1.4 ml dry triethylamine whereupon a solution of (endo)-9-methyl-9-azabicyclo[3.3.1]nonan-3-amine(1.1 g, 7 mmol) in 10 ml methylene chloride was added. This mixture was stirred at room temperature for 20 hours and washed with saturated sodium bicarbonate, water, and saturated sodium chloride. Evaporation of the solvent gave after trituration with acetone gave 1.5 g of the desired product. M.p. 189°–192° C.

EXAMPLE 25 a.

N-(2-Cyanophenyl)-N$^1$-(endo-9-methyl-9-azabicyclo-[3.3.1]non-3-yl)urea

To a solution of phosgene in toluene (12.6 ml, 1.9M) stirred at 0° C. under N$_2$ in 100 ml dry methylene chloride was added 2-aminobenzonitrtl (2.36 g, 20 mmol) in 75 ml dry methylene chloride and then 6.3 ml triethylamine. Upon addition the mixture was stirred at 0° C. for 10 min. whereupon a solution of (endo)-3-amino-9-methyl-9-azabicyclo-[3.3.1]nonan (3.55 g, 22.8 mmol) in 25 ml methylene chloride was added. This mixture was stirred at room temperature for 1 h, washed with saturated sodium tricarbonate, water and saturated sodium chloride, dried over magnesium sulphate and concentrated in vacuo. Trituration with ether gave 3.7 g of the desired product, m.p. 151°–159° C.

b.

N-(2-Hydroxyamidinophenyl)-N$^1$-(endo-9-methyl-9-azabicyclo[3.3.1]non-3-yl)urea To sodium (0.32 g, 14 mmol) dissolved in 10 ml dry methanol was added hydroxylamin hydrochloride (0.99 g, 14 mmol). The mixture was stirred at room temperature for 1 h and filtered. To the liltrate was added N-(2-cyanophenyl)-N$^1$-(endo-9-methyl-9-azabicyclo[3.3.1]-non-3-yl)urea (4.17 g, 14 mmol). After stirring the mixture at room temperature for 60 h ether was added to precipitate the desire product. Yield 3.75 g, m.p. 178°–180° C.

c. N-(Endo-9-methyl-9-azabicyclo[3.3.1]non-3-yl)-N$^1$-(2-(5-phenyl-1,2,4-oxadiazol-3-yl)-phenyl)urea, HCl To a solution of benzoylchloride (0.2 g, 1.4 mmol) in dry tetrahydrofuran (20 ml) stirred at 0° C. was added drowpise N-(2-hydroxyamidinophenyl)-N$^1$-(endo-9-methyl-9-azabicyclo [3.3.1]non-3-yl)urea (0.4 g, 1.25 mmol) dissolved in 4 ml dry DMF. After 1 h at room temperature the mixture as concentrated in vacuo and ether added to precipitate a semicrystalline product, which was purified by columnchromatography (silica gel; CH$_2$Cl$_2$, CH$_3$OH, 4:1 (v/v)). The resulting oil was dissolved in methylene chloride and the desired product precipitated by addition of HCl in ether. Yield 0.2 g, m.p. decomp. >90° C.

EXAMPLE 26

N-(2-(5-Ethyl-1,2,4-oxadiazol-3-yl)-phenyl)-N1-(endo-9-methyl-9-azabicyclo[3.3.1]non-3-yl)urea, HCl To a solution of propionic acid anhydride (160 mg, 1.23 mmol) in dry THF stirred at 0° C. was added dropwise N-(2-hydroxyamidinophenyl)-N1-(endo-9-methyl-9-azabicyclo [3.3.1]non-3-yl)urea (0.32 g, 1 mmol) dissolved in 2 ml dry DMF. After 1 h at room temperature 80 ml of ether was added to precipitate the product, which was purified by column chromatography (silica gel; methylene chloride, methanol; 4:1 (v/v)) to give the desired product. Yield: 200 mg, m.p. dec. >76° C.

EXAMPLE 27

N-(2-(5-Cyclopropyl-1,2,4-oxadiazol-3-yl)-phenyl)-N1-(endo-9-methyl-9-azabicyclo[3.3.1]non-3-yl)urea, HCl To a solution of cyclopropylcarbonyl chloride (70 mg, 0.7 mmol) in 20 ml dry THF stirred at 0° C. was added N-(2-hydroxyamidinophenyl)-N1-(endo-9-methyl-9-azabicyclo[3.3.1]-non-3-yl)urea (0.2 g, 0.6 mmol) dissolved in 2 ml dry DMF.

After 1 h at room temperature the precipitate was filtered off and refluxed in water (20 ml) for 5 h. The mixture was cooled to room temperature and extracted with $CH_2Cl_2$. The organic phase was dried over $MgSO_4$ and concentrated in vacuo. The product was dissolved in methanol and treated with HCl in methanol to give the desired product. Yield 110 mg, m.p. >85° C. decomp). MS (70 eV) m/z: 381 (52%, M+), 201 (20), 179 (37), 153 (30), 138 (50), 110 (75), 96 (100).

EXAMPLE 28

N-(2-(5-tertButyl-1,2,4-oxadiazol-3-yl)phenyl)-N1-(endo-9-methyl-9-azabicyclo[3.3.1]non-3-yl )urea, HCl To a solution of trimethylacetylchloride (0.2 g, 1.65 mmol) in 20 ml dry tetrahydrofurane stirred at 0° C. was added dropwise N-(2-hydroxyamidinophenyl)-N1-(endo-9-methyl-9-azabicyclo[3.3.1]non-3-yl)urea (0.4 g, 1.25 mmol) dissolved in 2 ml dry DMF. After 5 h at room temperature additional 0.6 g trimethylacaetyl chloride was added and stirring continued for 16 h. The solvent was evaporated off, and the product purified by column chromatography (silica gel; methylene chloride, methanol, 4:1 (v/v)). Yield 420 mg of the desired product as white crystals. M.p. decomp. >80° C.

EXAMPLE 29

N-(2-(5-Buryl-1,2,4-oxadiazol-3-yl)phenyl)-N 1-(endo-9-methyl-9-azabicyclo[3.3.1]non-3-yl)urea, HCl To a solution of pentanoic acid anhydride (0.26 g, 1.4 mmol) in dry THF (20 ml) stirred at 0° C. was added dropwise N-(2-hydroxyamidinophenyl)-N1-(endo-9-methyl-9-azabicyclo-[3.3.1]non-3-yl)urea (0.4 g, 1.25 mmol) dissolved in 2 ml dry DMF. After 1 h at room temperature 80 ml of ether was added to precipitate the product which was purified by column chromatography (silica gel; methylene chloride, methanol 4: 1 ( v/v ) ) to give 200 mg of the desired product. M.p. decomp. >80° C.

EXAMPLE 30

N-(2-(3-Cyclopropyl-1,2,4-oxadiazol-5-yl)-4-nitrophenyl)-N1-(endo-9-methyl-9-azabicyclo[3.3.1]non-3-yl)urea To a solution of phosgene in toluene (5.2 ml, 1.94M) and methylene chloride (25 ml) stirred under $N_2$ at 0° C. was added dropwise 5-(2-amino-4-nitrophenyl)-3-cyclopropyl-1,2,4-oxadiazol (1.5 g, 16 mmol) in 25 ml dry methylene chloride upon addition of 10 ml of the solution, 1.4 ml triethyl amine (10 mmol) was added. After addition was completed the mixture was stirred at 0° C. for 1 h and at room temperature for 2 h. The mixture was then concentrated in vacuo and redissolved in 25 ml methylene chloride and 1.4 ml triethyl amine. To this solution was added dropwise a solution of 3-amino-9-methyl-9-azabicyclo[3.3.1nonan (1.1 g, 7 mmol) in 10 ml methylene chloride and the mixture stirred for 72 h at room temperature. The mixture was then washed with saturated sodium bicarbonate, water, saturated sodium chloride, dried over magnesium sulphate and concentrated in vacuo. The product was purified by column chromatography (silica gel; methylene chloride, methanol, concentrated ammonium hydroxide; 90:10:0.5 (v/v/v)) to give the desired product as yellow crystalis after trituration with ethyl acetate. Yield 10 mg, m.p. 236°-237° C.

EXAMPLE 31

N-(2-(3-Methoxymethyl-1,2,4-oxadiazol-5-yl)phenyl-N1-(endo-9-methyl-9-azabicyclo[3.3.1]non-3-yl)urea, oxalate To a solution of phosgene in toluene (4.2 ml, 1.9M) stirred under $N_2$ at 0° C. was added dropwise a mixture of 5-(2-aminophenyl)-3-methoxymethyl-1,2,4-oxadiazol (0.8 g, 4 mmol) and 1.1 ml triethylamine in 15 ml dry methylene chloride. Upon addition the mixture was stirred at 0° C. for 1 h and at room temperature for 2 h. The mixture was then concentrated in vacuo and redissolved in 25 ml dry methylene chloride and 1.1 ml dry triethylamine, whereupon a solution of (endo)-3-amino-9-methyl-9-azabicyclo-[3.3.1]nonan (0.6 g, 4 mmol) in 10 ml methylen was added. This mixture was stirred at room temperature for 20 h and washed with saturated sodium bicarbonate, water, and saturated sodium chloride, dried over magnesium sulphate and concentrated in vacuo. The resulting oil was dissolved in acetone and treated with oxalic acid (0.5 g) in 2 ml acetone to precipitate the desired product. Yield 1.3 g, m.p. 110°-113° C.

EXAMPLE 32

N-(2-(3-Cyclopropyl-1,2,4-oxadiazol-5-yl)-3-methylphenyl)-N1-(endo-9-methyl-9-azabicyclo[3.3.1]non-3-yl)urea To a solution of phosgene in toluene (5.2 ml, 1.9M) stirred under $N_2$ at 0° C. was added dropwise a mixture of 5-(1-amino-3-methyl-2-phenyl)-3-cyclopropyl-1,2,4-oxadiazol (0.9 g, 4 mmol) and 1.4 ml dry triethylamin in 25 ml dry methylene chloride. Upon addition the mixture was stirred at 0° C. for 1 h and at room temperature for 2 h. The mixture was then dissolved in 25 ml dry methylene and 1.4 ml dry triethylamine, whereupon a solution of (endo)-3-amino-9-methyl-9-azabicyclo[3.3.1-]nonan (1.0 g, 6.5 mmol) in 10 ml methylene chloride was added. This mixture was stirred at room temperature for 20 h and washed with saturated sodium bicarbonate, water and saturated sodium chloride. Evaporation of the solvent gave after trituration with acetone 1.5 g of the desired product. M.p. 191°-192° C.

EXAMPLE 33

N-(2-Isopropoxyiminomethyl)-phenyl)-$N^1$-(endo-9-methyl-9-azabicyclo[3.3.1]non-3-yl)urea, oxalate To a solution of phosgene in toluene (10.5 ml, 1.93M) and methylene chloride (50 ml) stirred under $N_2$ at 0° C. was added dropwise 2-amino-N-isopropoxyiminomethylbenzene (1.4 g, 8 mmol) in methylene chloride (50 ml). After addition of 25 ml of this solution 2.8 ml triethylamine was added. Upon addition the mixture was stirred at 0° C. for 2 h and concentrated in vacuo. The mixture was then dissolved in 50 ml dry methylene chloride and 2.8 ml triethyl amine, whereupon (endo)-3-amino-9-methyl-9-azabicyclo[3.3.1]-nonane (1.5 g, 10 mmol) was added. After stirring for 24 h at room temperature the mixture was washed with saturated sodiumbicarbonate, water and saturated sodium chloride, dried over magnesium sulphate and evaporated. After trituration with acetone 1.8 g white crystals was isolated. Some of this product was dissolved in acetone and oxalic acid added to precipitate the desired product. M.p. 133°-134° C.

EXAMPLE 34

N-(2-Isopropoxyiminomethyl)-phenyl)-$N^1$-(endo-8-methyl-8-azabicyclo[3.3.1]oct-3-yl)urea, oxalate To a solution of phosgene in toluene (10.5 ml, 1.93M) and methylene chloride (50 ml) stirred under $N_2$ at 0° C. was added dropwise 2-amino-N-isopropoxyiminomethylbenzene (1.4 g, 8 mmol) in methylene chloride (50 ml). After addition of 25 ml of this solution 2.8 ml triethylamine was added. Upon addition the mixture was stirred at 0° C. for 2 h and concentrated in vacuo. The mixture was then dissolved in 50 ml dry methylene chloride and 2.8 ml triethyl amine, whereupon (endo)-3-amino-8-methyl-8-azabicyclo-[3.2.1]octane (1.4 g, 10 mmol) was added. After stirring for 5 days at room temperature the mixture was washed with saturated sodiumbicarbonate, water and saturated sodium chloride, dried over magnesium sulphate and evaporated. The resulting oil was purified by column chromatography (silica gel; methylene chloride, methanol, concentrated ammonium hydroxide; 80:20:0.5 (v/v/v/)). This product was dissolved in acetone and oxalic acid (300 mg) in 5 ml acetone added to precipitate the desired product. Yield 1.1 g. M.p. 117°-119° C.

I claim:

1. A compound of formula I:

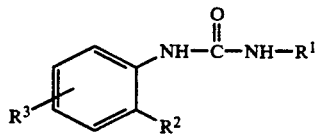

wherein
$R^1$ is a group of formula II

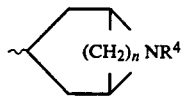

wherein n is 2 or 3 and $R^4$ is H or $C_{1-7}$-alkyl;

$R^2$ is a 1,2,4-oxadiazole optionally substituted with $C_{1-8}$-alkyl, $C_{3-7}$-cycloalkyl or phenyl; or $R^2$ is —C-(—$R^6$)=N—O—$R^7$, wherein $R^6$ is hydrogen or methyl and $R^7$ is $C_{1-6}$-alkyl which may be substituted with $C_{3-7}$-cycloalkyl; and $R^3$ is hydrogen, methyl, nitro or halogen; or a pharmaceutically acceptable salt thereof.

2. A compound according to claim 1, wherein $R^3$ is hydrogen.

3. A compound according to claim 1, wherein $R^4$ is methyl.

4. A compound according to claim 1, wherein $R^6$ is hydrogen.

5. A compound according to claim 1, wherein $R^3$ is hydrogen, $R^4$ is methyl and $R^6$ is hydrogen.

6. A compound according to claim 1 which is
N-(endo-8-methyl-8-azabicyclo[3.2.1]oct-3-yl)-$N^1$-(2-(N-cyclopropylmethoxyiminomethyl)phenyl)urea;
N-(endo-8-methyl-8-azabicyclo[3.2.1]oct-3-yl)-$N^1$-(2-(N-ethoxyiminomethyl)phenyl)urea;
N-(2-(N-methoxyiminomethyl)phenyl-$N^1$-(endo-8-methyl-8-azabicyclo[3.2.1]oct-3-yl)urea;
N-(2-isopropoxyiminomethyl)phenyl-$N^1$-(endo-8-methyl-8-azabicyclo[3.2.1]oct-3yl)urea; or
a pharmaceutically acceptable salt thereof.

7. A compound according to claim 1 which is
N-(2-(N-methoxyiminomethyl)phenyl-$N^1$-(endo-9-methyl-9-azabicyclo[3.3.1]non-3-yl)urea;
N-(2-isopropoxyiminomethyl)phenyl-$N^1$-(endo-9-methyl-9-azabicyclo[3.3.1]non-3-yl)urea; or
a pharmaceutically acceptable salt thereof.

8. a compound according to claim 1 which is
N-(2-(3-cyclopropyl-1,2,4-oxadiazol-5-yl)phenyl)-$N^1$-(endo-8methyl-8-azabicyclo[3.2.1]oct-3-yl)urea;
N-(endo-8-methyl-8-azabicyclo[3.2.1]oct-3-yl)-$N^1$-(2-(3-methyl-1,2,4-oxadiazol-5-yl)phenyl)urea;
N-(2-(3-butyl-1,3,4-oxadiazol-5-yl)phenyl)-$N^1$-(endo-8-methyl-8-azabicyclo[3.2.1]oct-3-yl)urea;
N-(endo-8-methyl-8-azabicyclo[3.2.1]oct-3-yl)$N^1$-(2-(3-phenyl-1,2,4-oxadiazol-5-yl)phenyl)urea; or
a pharmaceutically acceptable salt thereof.

9. A compound according to claim 1 which is
N-(2-(3-cyclopropyl-1,2,4-oxadiazol-5-yl)phenyl)-$N^1$-(endo-9-methyl-9-azabicyclo[3.3.1]non-3-yl)urea;
N-(endo-9-methyl-9-azabicyclo[3.3.1]non-3-yl)-$N^1$-(2-(3-phenyl-1,2,4-oxadiazol-5-yl)phenyl)urea;
N-(2-(3-butyl-1,2,4-oxadiazol-5-yl)phenyl)-$N^1$-(endo-9-methyl-9-azabicyclo[3.3.1]non-3-yl)urea;
N-(3-chloro-2-(3-cyclopropyl-1,2,4-oxadiazol-5-yl)phenyl)-$N^1$-(endo-9-methyl-9-azabicyclo[3.3.1]-non-3-yl)urea;
N-(5-chloro-2-(3-cyclopropyl-1,2,4-oxadiazol-5-yl)phenyl)-$N^1$-(endo-9-methyl-9-azabicyclo[3.3.1]-non-3-yl)urea;
N-(endo-9-methyl-9-azabicyclo[3.3.1]non-3-yl)-$N^1$-(2-(5-phenyl-1,2,4-oxadiazol-3-yl)phenyl)urea;
N-(2-(3-cyclopropyl-1,2,4-oxadiazol-3-yl)-3-methylphenyl)-$N^1$-(endo-9-methyl-9-azabicyclo[3.3.1]non-3-yl)urea; or
a pharamaceutically acceptable salt thereof.

10. A compound which is N-(2-(3-methoxymethyl-1,2,4-oxadiazol-5-yl)phenyl)-$N^1$-(endo-9-methyl-9-azabicyclo[3.3.1]non-3-yl)urea or a pharmaceutically acceptable salt thereof.

11. A pharmaceutical composition for use in treating a central nervous system ailment related to the 5-$HT_3$ receptor system comprising an effective amount of a compound according to claim 1 and a pharmaceutically acceptable carrier or diluent.

12. The pharmaceutical composition according to claim 11 which contains between 0.1 mg and 250 mg of the compound per dose unit.

13. A method of treating a central nervous system ailment related to the 5-HT$_3$ receptor system in a subject in need thereof comprising administering an effective amount of a compound according to claim 1.

14. A method of treating a central nervous system ailment related to the 5-HT$_3$ receptor system, in a subject in need thereof comprising administering a pharmaceutical composition according to claim 11.

* * * * *